United States Patent [19]
Georger et al.

[11] Patent Number: 5,919,177
[45] Date of Patent: Jul. 6, 1999

[54] PERMEABLE FIBER-LIKE FILM COATED NONWOVEN

[75] Inventors: William Anthony Georger, Neenah, Wis.; Mark Bruce Majors, Cumming; Gregory Alan Zelazoski, Woodstock, both of Ga.

[73] Assignee: Kimberly-Clark Worldwide, Inc., Neenah, Wis.

[21] Appl. No.: 08/825,452

[22] Filed: Mar. 28, 1997

[51] Int. Cl.$^6$ ............................. A61F 13/15; B32B 31/00; B32B 3/10

[52] U.S. Cl. ........................ 604/367; 604/383; 604/378; 156/84; 156/85; 156/163; 156/229; 428/131; 428/137; 428/152

[58] Field of Search ................................. 604/367, 378, 604/385.1, 383; 156/84, 85, 163, 229; 428/131, 137, 152

[56] References Cited

U.S. PATENT DOCUMENTS

| | | | |
|---|---|---|---|
| H1575 | 8/1996 | Daugherty et al. | 604/378 |
| T857,038 | 12/1968 | Zeisberg | 161/109 |
| 2,877,765 | 3/1959 | Bunyan | 128/156 |
| 2,898,910 | 8/1959 | Gross et al. | 128/156 |
| 2,923,298 | 2/1960 | Dockstader et al. | 128/296 |
| 2,940,868 | 6/1960 | Patchell | 117/38 |
| 3,331,728 | 7/1967 | Lane | 161/112 |
| 3,338,992 | 8/1967 | Kinney | 264/24 |
| 3,341,394 | 9/1967 | Kinney | 161/72 |
| 3,399,672 | 9/1968 | Crowe, Jr. et al. | 128/156 |
| 3,502,763 | 3/1970 | Hartmann | 264/210 |
| 3,542,615 | 11/1970 | Dobo et al. | 156/181 |
| 3,654,060 | 4/1972 | Goldman | 161/112 |
| 3,655,501 | 4/1972 | Tesch | 161/109 |
| 3,676,242 | 7/1972 | Prentice | 156/62.4 |
| 3,690,977 | 9/1972 | Loft et al. | 156/167 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,906,130 | 9/1975 | Tsurumi et al. | 428/131 |
| 3,929,135 | 12/1975 | Thompson | 128/287 |
| 3,967,623 | 7/1976 | Butterworth et al. | 128/287 |
| 4,041,203 | 8/1977 | Brock et al. | 428/157 |
| 4,100,324 | 7/1978 | Anderson et al. | 428/288 |
| 4,322,450 | 3/1982 | Gray, III et al. | 427/44 |
| 4,340,563 | 7/1982 | Appel et al. | 264/518 |
| 4,469,734 | 9/1984 | Minto et al. | 428/134 |
| 4,518,643 | 5/1985 | Francis | 428/131 |
| 4,608,292 | 8/1986 | Lassen | 428/131 |
| 4,684,568 | 8/1987 | Lou | 428/265 |
| 4,726,976 | 2/1988 | Karami et al. | 428/137 |
| 4,735,843 | 4/1988 | Noda | 428/137 |

(List continued on next page.)

FOREIGN PATENT DOCUMENTS

| | | | |
|---|---|---|---|
| 0 207 904 | 1/1987 | European Pat. Off. | |
| 0 598 970 | 1/1994 | European Pat. Off. | B26F 1/24 |
| 0 596 532 | 5/1994 | European Pat. Off. | |
| 0 749 739 | 12/1996 | European Pat. Off. | |
| 0 749 740 | 12/1996 | European Pat. Off. | |
| 26 14 160 | 10/1977 | Germany | D04H 13/00 |
| 2 286 558 | 8/1995 | WIPO | B32B 27/12 |
| 96/10979 | 4/1996 | WIPO | |
| 96/26697 | 9/1996 | WIPO | |
| 96/39109 | 12/1996 | WIPO | |

OTHER PUBLICATIONS

PCT/US 98/ 05018 Search Report, No. of p.–8.

*Primary Examiner*—Robert A. Clarke
*Attorney, Agent, or Firm*—Lisa J. Moyles; James B. Robinson

[57] ABSTRACT

There is provided a cushioned absorbent material which may be used as a bodyside liner for a personal care product which is made from a lofty nonwoven fabric onto which is extruded a film to form a laminate. The laminate is then apertured and has an 8 cc intake rate of at most 20 sec and a rewet of less than 1 gm. Such a liner may be used in personal care products like diapers, training pants, feminine hygiene products, absorbent underpants, adult incontinence products, and the like.

21 Claims, 1 Drawing Sheet

U.S. PATENT DOCUMENTS

| | | | |
|---|---|---|---|
| 4,781,962 | 11/1988 | Zamarripa et al. | 428/138 |
| 4,854,984 | 8/1989 | Ball et al. | 156/73.5 |
| 4,898,761 | 2/1990 | Dunaway et al. | 428/137 |
| 4,919,738 | 4/1990 | Ball et al. | 156/73.5 |
| 5,030,500 | 7/1991 | Perdelwitz, Jr. et al. | 428/137 |
| 5,057,361 | 10/1991 | Sayovitz et al. | 428/290 |
| 5,085,914 | 2/1992 | Perdelwitz et al. | 428/137 |
| 5,108,827 | 4/1992 | Gessner | 428/219 |
| 5,171,238 | 12/1992 | Kajander | 604/383 |
| 5,277,976 | 1/1994 | Hogle et al. | 428/397 |
| 5,336,552 | 8/1994 | Strack et al. | 428/224 |
| 5,368,910 | 11/1994 | Langdon | 428/137 |
| 5,370,764 | 12/1994 | Alikhan | 156/553 |
| 5,382,400 | 1/1995 | Pike et al. | 264/168 |
| 5,443,886 | 8/1995 | Cohen et al. | 428/131 |
| 5,536,555 | 7/1996 | Zelazoski et al. | 428/138 |
| 5,643,240 | 7/1997 | Jackson et al. | 604/378 |

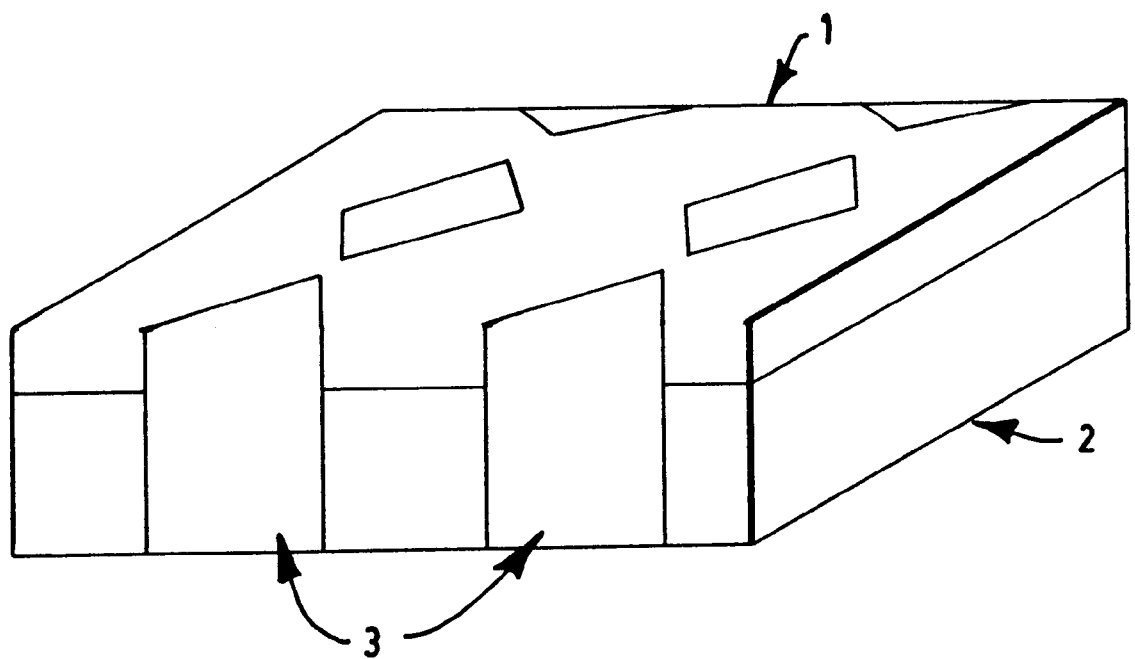

PERMEABLE FIBER-LIKE FILM COATED NONWOVEN

BACKGROUND OF THE INVENTION

Cover materials for personal care products should transmit liquid through from the wearer to the layers below the cover (or liner) material where the liquid may be absorbed or distributed to other areas. Liner materials preferably have low stain and low rewet surfaces in order to reduce the amount of liquid retained in the liner material itself. Apertured films are known in the art for use as liners because of their reduced staining and low rewetting. They do not, however, provide the softness and comfort of fibrous nonwoven liners. There remains, therefore, a need for a liner which provides the advantages of a film based liner, while also being soft and comfortable for the wearer.

One objective of this invention is the provision of a cushioned absorbent material which may be used as a liner which has low staining and rewetting and is soft and comfortable for the wearer. A further objective is for such a liner to also have greater strength than a film liner, and further, to enhance fluid handling functionality.

SUMMARY OF THE INVENTION

The objects of this invention are achieved by a cushioned absorbent material which may be used as a liner material which is made from a film and a nonwoven fabric where the film is extruded directly onto the nonwoven fabric to form a laminate, thereby providing fiber-like topography and feel to the film. The film/nonwoven fabric laminate is made permeable by aperturing the laminate. The nonwoven must be a high loft type nonwoven in order to provide the desirable fluid handling functionality.

BRIEF DESCRIPTION OF THE DRAWING

The FIGURE is a cut-away drawing of a film/nonwoven fabric laminate of the invention where the film 1 is laminated to the nonwoven fabric 2 and the laminate has apertures 3.

DEFINITIONS

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than 90° are designated "nonwettable" or hydrophobic.

"Layer" when used in the singular can have the dual meaning of a single element or a plurality of elements.

"Liquid" means a nongaseous substance and/or material that flows and can assume the interior shape of a container into which it is poured or placed.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 31.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

"Lofty" refers to the thickness and density of a nonwoven fabric and means a fabric which provides improved fluid functionality and tactile properties when used as a substrate in an apertured film coated material. Improvement may be seen in materials having a thickness or bulk of at least about 0.03 inches (0.76 mm) and preferably about 0.05 inches (1.3 mm) and a density between about 0.03 g/cc and about 0.07 g/cc, preferably about 0.05 g/cc.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

As used herein, the term "machine direction" or MD means the length of a fabric in the direction in which it is produced. The term "cross machine direction" or CD means the width of fabric, i.e. a direction generally perpendicular to the MD.

"Conjugate fibers" refers to fibers which have been formed from at least two polymer sources extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught, for example, in U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. Nos. 5,277,976 to Hogle et al. which describes fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner.

"Bonded carded web" refers to webs that are made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" is a well known process by which a fibrous nonwoven layer can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

As used herein, through-air bonding means a process of bonding a fiber web in which air which is sufficiently hot to melt the polymers of which the fibers of the web are made is forced through the web. The air velocity is between 100 and 500 feet per minute and the dwell time may be as long as 6 seconds. The melting and resolidification of the polymer provides the bonding.

"Personal care product" means diapers, training pants, absorbent underpants, adult incontinence products, and feminine hygiene products.

TEST METHODS

The density of a material is calculated by dividing the weight per unit area of a sample in grams per square meter (gsm) by the thickness of the sample in millimeters (mm) at 68.9 Pascals and multiplying the result by 0.001 to convert the value to grams per cubic centimeter (g/cc). A total of three samples would be evaluated and averaged for the density values.

Air permeability was measured using the Frazier porosity test. Air permeability is the rate of air flow through a material under a pressure differential between two fabric surfaces. Samples were tested on a Frazier Air Permeability Tester available from Frazier Precision Instrument Company of Gaithersburg, Md. The procedures used conformed to the specifications of Method 5450, Federal Test Methods Standard 191A except that the specimen size was 8 inches×8 inches (20.3×20.3 cm) rather than 7 inches×7 inches (17.8× 17.8 cm). The larger size made it possible to ensure that all sides of the specimen extended well beyond the retaining ring and facilitated clamping of the specimen securely and evenly across the orifice. In the procedure, air was drawn through the specimen and a calibrated orifice using a suction fan. By controlling the speed of the fan, the rate of air flow through the fabric was adjusted to obtain a pressure differential of 0.51 inches (13 mm) of water between the two surfaces. The amount of air flowing through the specimen was determined from the drop in pressure across a calibrated orifice as indicated by a vertical oil manometer. This reading was converted to an air flow rate using a conversion table provided by the manufacturer of the instrument. The results were expressed in cubic feet of air per square foot of specimen per minute or in cubic centimeters per square centimeter per second. The higher the number, the more permeable or porous the material.

The absorption time test indicated the intake rate for a material using 8 cc of synthetic menstrual fluid. A 3 inch by 7 inch sample of the test material was insulted with 10 cc of synthetic menstrual fluid delivered from a fluid reservoir having a 2 inch by 0.5 inch delivery slot. The time to absorb 8 cc of fluid was then measured in seconds. A lower absorption time as measured in seconds was an indication of a faster intake rate for the particular material.

Once a material has been insulted, it was also important to measure the amount of rewet that took place. The test specimen is placed on top of a two layer absorbent core with the nonwoven side adjacent the absorbent to simulate the cover material of a personal care absorbent article, in this case a feminine pad or sanitary napkin. The top, body side layer of the core was a 425 gsm fluff with a density of about 0.07 g/cc and the baffle side layer was a 470 gsm fluff with a density of about 0.094 g/cc. The baffle side was embossed. Ten cubic centimeters of the synthetic menstrual fluid were delivered to the test specimen from a reservoir having a 2 inch by 0.5 inch delivery slot. Next a blotter was placed on top of the specimen and one pound per square inch of pressure was applied for a period of 3 minutes. After the 3 minute interval, the blotter paper was removed and weighed and the amount of menstrual fluid absorbed by the blotter paper was measured in grams. Higher values were an indication of a greater degree of rewet for the particular material tested. Additional discussion of these tests may be found in U.S. Pat. No. 5,536,555, commonly assigned.

To measure the Starrett Bulk or caliper of the material, which relates to the thickness of the material, five inch by five inch (127 millimeter×127 millimeter) samples of material were compressed under a load of 0.05 pounds per square inch and the thickness of the material was measured while the sample was under compression. Higher numbers indicated thicker, more bulky materials.

DETAILED DESCRIPTION OF THE INVENTION

Absorbent products generally have a liner which goes against the wearer, a backsheet which is the most exterior layer, and may also contain other layers.

The liner is sometimes referred to as a bodyside liner, cover sheet or topsheet and may be adjacent to a surge material. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating. Various materials have been used in forming a bodyside liner, including apertured plastic films, woven fabrics, nonwoven webs, porous foams, reticulated foams and the like. The liner can be surface treated with a selected amount of surfactant, such as about 0.28% Triton X-102 surfactant, or otherwise processed to impart the desired level of wettability and hydrophilicity. If a surfactant is used, it can be an internal additive or applied to the web by any conventional means, such as spraying, printing, dipping, brush coating and the like.

The backsheet is sometimes referred to as the outer cover and is the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the personal care product. Other alternative constructions for outer cover include woven or nonwoven fibrous webs that have been constructed or treated to impart the desired level of liquid impermeability, or laminates formed of a woven or nonwoven fabric and thermoplastic film.

In addition to the liner and backsheet performing the functions described above, traditional absorbent systems for personal care products may be generalized as having the functions of surge control and containment (retention) or SC.

The surge control function is to quickly accept the incoming insult and either absorb, hold, channel or otherwise manage the liquid so that it does not leak outside the article. A surge layer may also be referred to as an intake layer, transfer layer, transport layer and the like and is most typically interposed between and in intimate, liquid communicating contact with the bodyside liner and another layer such as a retention layer to which it may be attached.

The containment or retention function is to absorb the insult quickly and efficiently. A material providing retention functionality should be capable of pulling liquid from the distribution layer and absorbing liquid without significant "gel blocking" or blocking of penetration of liquid further into the absorbent by the expansion of the outer layers of absorbent. Retention is often provided by absorbent compositions such as those containing high rate superabsorbent polymers such as blends of polyacrylate superabsorbent and fluff. These materials rapidly absorb and hold liquid.

In addition to the surge control and containment functions in traditional absorbent systems, recent work has introduced another function which may be a separate layer interposed between the S and C layers or may be incorporated into existing materials. This new function is a distribution function, producing a system with surge control, distribution and containment or "SDC".

The distribution function is to move fluid from the point of initial deposition to where storage is desired. Distribution should preferably take place at an acceptable speed such that the target insult area, generally the crotch area, is ready for the next insult. The time between insults can range from just a few minutes to hours, generally depending on the age of the wearer. Materials from which the distribution layer may be made include woven fabrics and nonwoven webs. For example, a distribution layer may be a nonwoven fabric layer composed of a meltblown or spunbond web of polyolefin filaments.

The advanced liner described herein provides the traditional liner function of isolating the wearer's skin from liquids and also provides a number of other beneficial functions which combine some features of surge control and distribution as well. Such a liner gives design flexibility and may allow the production of thinner, more comfortable and lower cost personal care products.

The inventors have found that cushioned absorbent material comprising an apertured, film coated lofty nonwoven fabric provides excellent fluid intake while retaining a low rewet value (less than 1 gm) and having good tensile strength.

EXAMPLE

As one embodiment, an apertured film coated lofty nonwoven fabric laminate was produced by extrusion coating a 0.75 mil (0.02 mm) low density polyethylene (LDPE) film onto a polypropylenelpolyethylene side-by-side bicomponent nonwoven fabric. By forming the film directly onto the nonwoven fabric, fiber-like characteristics were imparted to the film.

The film was made from polyethylene supplied by Quantum Chemical Co. of Wallingford, Conn. under the designation NA206. The film contained about 12 weight percent of titanium dioxide to mask stains and reduce gloss.

The Nonwoven fabric was a 50/50 side-by-side conjugate fiber web made from polyethylene supplied by the Dow Chemical Co. of Midland, Mich. under the designation Aspun® 6811A and polypropylene supplied by the Exxon Chemical Co. of Houston, Tex. under the designation Escoren® PD-3445. The nonwoven fabric had a basis weight of about 1 osy (34 gsm) and was made from 5 denier, through-air bonded, high crimp fibers produced by the spunbond process as described in U.S. Pat. No. 5,382,400. The spunbond fabric was stretched about 20 percent in the machine direction (MD) as the film was applied in order to further enhance fiber-like appearance and the thickness of the laminate. The nonwoven fabric had a thickness of about 0.07 in (1.8 mm) and a density of about 0.03 g/cc.

The laminate was apertured using a male pattern roll and a smooth steel anvil roll using a 10:1 surface speed differential between the rollers which were at 200° F. (93° C.) and 160 fpm (49 meter/min) and 170° F. (77° C.) and 15 fpm (4.6 meters/min) respectively. Aperturing conditions were chosen to maximize the openness and porosity of the laminate while minimizing the densification of the web. If too much heat and pressure is used, the loft and functionality of the web will be lost. This method of aperturing is also discussed in allowed U.S. patent application Ser. No. 08/620,865, hereby incorporated by reference in its entirety.

After aperturing, the nonwoven side of the laminate was spray treated with an aqueous solution containing 0.3 weight percent of a surfactant designated Y-12488 from Osi Specialties, Inc. of Danbury, Conn. which is a polyalkylene oxidemodified polydimethylsiloxane non-ionic surfactant wetting agent.

This apertured laminate was evaluated for use as a sanitary napkin cover and exhibited a soft, cloth-like surface and excellent fluid handling characteristics. The data in the Table indicate that the laminate was very open with a porosity of 455 standard cubic feet per minute (scfm), a caliper of 0.038 inches (0.97 mm) and had an intake of 14.2 seconds and a rewet of 0.4 grams.

The standard used for comparison in the Table is an apertured film made with the same polyethylene and titanium dioxide as the Example. The film was apertured using the same pattern roll moving at about 51 fpm (15.5 m/min) and an anvil roll moving at about 25 fpm (7.62 m/min) with temperatures of 195° F. (91° C.) and 170° F. (77° C.) respectively. The nip pressure was about 39 psi.

TABLE

|  | Standard | Example |
| --- | --- | --- |
| Porosity (scfm) | 715 | 455 |
| Caliper (inches) | 0.021 | 0.038 |
| MD tensile strength (lb.) | 0.59 | 0.83 |
| CD tensile strength (lb.) | 0.54 | 0.39 |
| Adhesion (kg) | NA | 1.9 |
| 8 cc intake (sec) | 13.3 | 14.2 |
| Rewet (gms) | 1.22 | 0.43 |

Note that the tensile results have been normalized to a 1 mil film thickness equivalent.

Although a specific embodiment of the invention is described, it is not intended to limit the scope of the invention. Various polymers, film coating methods, aperturing methods, etc., may be used and still be within the contemplated range of the invention.

The film coating should be selected to provide the required laminate softness, opacity, strength, adhesion and cost. In general, a film may range from 0.25 to 3 mil (0.006 mm to 0.076 mm). Polyethylene is preferred because of its relatively lower cost and its soft hand though any polymer capable of being made into a film may be used.

The lofty nonwoven should be chosen to meet laminate caliper and density requirements for permeability, rewet, etc. needs. Desirably the nonwoven should have a thickness or bulk of at between about 0.05 inches (1.27 mm) and 0.11 in (2.8 mm) and preferably about 0.085 inches (2.16 mm), and a density between about 0.043 g/cc and about 0.019 g/cc, preferably about 0.025 g/cc, prior to lamination and aperturing. Lamination and aperturing may result in some densification.

Generally the nonwoven basis weights can range from 0.5 to 5 osy (17 gsm–174 gsm) and microfiber sizes from less than 10 microns to 6 denier. The nonwoven may be made according to a number of processes including meltblown, spunbond, bonded carded web, airlaid. Side-by-side conjugate fibers are recommended since such fibers may be crimped and such crimping aids in producing a lofty web. Polyolefins are well suited for fiber production because of their low cost and ease of processing and many polyolefins are available for fiber production. Polyethylenes such as Dow Chemical's ASPUN® 6811A linear low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's Escorene® PD 3445 polypropylene and Montell Chemical Co.'s PF-304. Many other polyolefins are commercially available.

The coating method is preferably extrusion coating though other methods like spray, print and adhesive may be used.

The aperturing method preferred is the one described in the Example, however, other methods like hot pin aperturing, needling, male/female perforating/embossing and hydro-aperturing may be used.

The aperturing method used in the Example may be carried out at a range of temperatures and relative roller rotational speeds. U.S. Pat. No. 4,781,962 describes aperturing wherein the surface speed differential between the rollers is between 0 and 50 percent. Further, though the pattern roll is generally rotated at a higher speed than the anvil roll, acceptable apertured laminates may be produced by rotating the anvil roll faster than the pattern roll. Two patterned rolls, also known as male to male engraving, may also be used. In any method, the aperturing pattern should be designed to provide at least 20 percent open area.

As can be seen from the above description, there is herein provided a cushioned absorbent material which may be used as a liner, having superior strength and fluid handling functionality to other known liners and which is soft and comfortable for the wearer. This provides a great advance in absorbent technology and personal care product design. Improved liners allow for more narrow, and therefore more comfortable, personal care products. In diapers, for example, a narrow crotch design is one with a width of less than about 7.6 cm.

In addition to its use as a liner, the cushioned absorbent material of this invention may find utility as a more fiber and lint-free fabric for surgical drapes and gowns, as pads for clean room countertops and other applications where low lint and cushioning are important.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A cushioned absorbent material comprising a lofty nonwoven fabric onto which is directly extruded a film to form a laminate, and wherein said laminate is apertured and has an 8 cc intake rate of at most 20 sec and a rewet of less than 1 gm.

2. The material of claim 1 wherein said nonwoven has a thickness of at least about 0.03 inches (0.76 mm) and a density between about 0.03 g/cc and about 0.07 g/cc.

3. The material of claim 2 wherein said nonwoven has a thickness of about 0.05 inches (1.3 mm) and a density of about 0.05 g/cc.

4. The material of claim 1 wherein said aperturing results in said laminate having at least 20 percent open area.

5. The material of claim 1 wherein said film comprises a polyolefin.

6. The material of claim 5 wherein said film further comprises titanium dioxide.

7. The material of claim 1 wherein said nonwoven fabric is comprised of polyolefin fibers.

8. The material of claim 1 wherein said nonwoven fabric is comprised of conjugate fibers.

9. The fabric of claim 8 wherein said conjugate fibers are comprised of polyethylene and polypropylene.

10. The material of claim 1 wherein said nonwoven fabric is comprised of biconstituent fibers.

11. A personal care product selected from the group consisting of diapers, training pants, absorbent underpants, adult incontinence products and feminine hygiene products comprising the material of claim 1.

12. The product of claim 11 wherein said personal care product is a feminine hygiene product and said material is a liner.

13. The product of claim 11 wherein said personal care product is an adult incontinence product and said material is a liner.

14. The product of claim 11 wherein said personal care product is a diaper and said material is a liner.

15. The diaper of claim 14 having a crotch width of at most 7.6 cm.

16. A process of making a bodyside liner for a personal care product comprising the steps of:

stretching a lofty nonwoven fabric;

extruding a film directly onto said stretched nonwoven fabric to form a laminate;

aperturing said laminate;

whereby said laminate has an 8 cc intake rate of at most 20 sec and a rewet of less than 1 gm.

17. The process of claim 16 wherein said nonwoven has a thickness of at least about 0.76 mm and a density of at least about 0.03 g/cc.

18. The process of claim 16 wherein said film has a thickness of from about 0.006 to about 0.076 mm.

19. The process of claim 16 wherein said aperturing results in said laminate having at least 20 percent open area.

20. The process of claim 16 wherein said film contains titanium dioxide.

21. The process of claim 16 wherein said stretching step comprises stretching said lofty nonwoven fabric by at least about 20 percent in the machine direction.

* * * * *